United States Patent [19]

Stuart et al.

[11] Patent Number: 4,735,899

[45] Date of Patent: Apr. 5, 1988

[54] DETECTION OF AIRBORNE MICROORGANISMS

[75] Inventors: David G. Stuart, Kennebunk; John M. Eagleson, Jr., Kennebunkport, both of Me.

[73] Assignee: The Baker Company, Inc., Sanford, Me.

[21] Appl. No.: 710,325

[22] Filed: Mar. 11, 1985

[51] Int. Cl.$^4$ .................. C12Q 1/02; C12Q 1/22
[52] U.S. Cl. ............................ 435/29; 435/31; 435/810; 436/3
[58] Field of Search ............ 435/4, 29, 31, 32, 810, 435/34; 436/10, 519, 531, 533, 534, 3; 73/865.9, 866, 40.7

[56] References Cited

U.S. PATENT DOCUMENTS

| | | | |
|---|---|---|---|
| H000,110 | 8/1986 | Barditch et al. | 435/34 X |
| 2,672,431 | 3/1954 | Goetz | 195/139 |
| 3,001,914 | 9/1961 | Andersen | 195/103.5 |
| 3,127,329 | 3/1964 | Andersen | 195/103.5 |
| 3,128,239 | 4/1964 | Page | 195/127 |
| 3,129,144 | 4/1964 | Page et al. | 195/127 |
| 3,232,094 | 2/1966 | Teschner | 73/28 |
| 3,234,045 | 2/1966 | Larsen | 73/40.7 X |
| 3,458,284 | 7/1969 | Rich et al. | 23/230 |
| 3,522,724 | 8/1970 | Knab | 73/40.7 |
| 3,551,295 | 12/1970 | Dyer | 195/103.5 |
| 3,576,721 | 4/1971 | Mason | 195/139 |
| 3,690,837 | 9/1972 | Witz et al. | 23/254 |
| 3,751,340 | 8/1973 | Witz | 435/34 X |
| 3,902,971 | 9/1975 | Fletcher et al. | 195/103.5 |
| 3,956,070 | 5/1976 | Kenyon | 195/103.5 |
| 3,960,001 | 6/1976 | Hayes | 73/40.7 |
| 3,972,226 | 8/1976 | Rountree et al. | 73/28 |
| 3,980,524 | 9/1976 | Reuter | 195/139 |
| 4,014,747 | 3/1977 | Kenyon | 195/127 |
| 4,073,686 | 2/1978 | Adams | 195/2 |
| 4,092,221 | 5/1978 | Schlichting, Jr. | 195/127 |
| 4,381,664 | 5/1983 | Clark et al. | 73/40.7 |
| 4,402,214 | 9/1983 | Morgan et al. | 73/40.7 |

*Primary Examiner*—Robert J. Warden
*Assistant Examiner*—Randall E. Deck
*Attorney, Agent, or Firm*—Lahive & Cockfield

[57] ABSTRACT

Disclosed is a process and test kit for determining the reliability of a barrier to microorganism passage. In accordance with the process, a multiplicity of non-self replicating particles is introduced into a first gas volume, disposed on one side of a barrier to particle movement, and particle traps are placed in a second gas volume on the other side of the barrier. The particles carry a marker substance such as a toxin for a selected microorganism or a component needed for growth of a selected microorganism. The barrier is operated and the contents of the trap are assayed for the amount of the marker substance present in association with particles which crossed the barrier by adding the marker substance in the trap to a culture of the selected microorganism and detecting the effect of the marker substance on the culture. Finally, the results of the assay are compared to a standard to determine the number of trapped particles which crossed the barrier. The process is capable of detecting the presence of less than 10 and as few as a single one of the particles.

21 Claims, 1 Drawing Sheet

DETECTION OF AIRBORNE MICROORGANISMS

BACKGROUND OF THE INVENTION

This invention relates to a process for determining whether microorganisms, that is, airborne microorganisms such as viruses, spores, bacterial cells, yeast cells, and the like, are escaping from equipment or building installations designed to confine them, and if so, for detecting the general location of the leak and its magnitude.

Systems for distributing air such as air conditioning and forced hot air heating systems potentially provide an airstream which can carry unwanted microorganisms and other particles into living space, areas devoted to health care, clean rooms used to produce solid state devices or pure microbiological cultures, and other areas. Biological containment cabinets and glove boxes are designed to provide a barrier, e.g., and air curtain, between a work space within the hood and the ambient environment. Improper installation, maintenance, design, or construction of such devices may lead to improper functioning of an air curtain, seal, filter, or the like, and may result in contamination of the environment or workspace with foreign, live microorganisms.

While the injection into such a system of a smoke, fog or other visually detectable fluid such as a colored gas may be used to detect air leaks, this approach cannot detect the escape of extremely small numbers of airborne microorganisms with the sensitivity required in the more demanding problems of biological containment. For example, the escape of even a single viable bacterial spore or other viable microorganism potentially can destroy a costly and tedious genetic engineering effort or lead to a health risk. Consequently, the National Sanitation Foundation (NSF) requires efficacy testing of prototype biological containment hoods.

The NSF currently has accepted a "Bacterial Aerosol Tracer" test as a minimal efficacy test for biological containment hoods. To conduct the test, a technician sprays a fog of viable microorganisms, typically bacterial spores, into the containment hood while the hood is in operation. Typically $1 \times 10^8$ to $8 \times 10^8$ spores are introduced over a five minute period. Particle traps are situated on the outside of the air curtains and at other locations where there is a possibility of particle escape. The technician subsequently adds the contents of the traps to a medium designed to promote growth of the test microorganism, and after a suitable incubation period, inspects the culture vessels for colonies of bacteria. Because each spore can reproduce repeatedly to form a detectable bacterial colony, this test enables detection of the escape of even a single spore. Generally, the detection of 10 or more microorganisms is indicative that the hood is not functioning properly.

While the foregoing procedure works well, it cannot be used at the site of installation of a containment hood because of the unacceptable risk of contaminating the site with foreign microorganisms. Its use in testing air moving systems associated with clean rooms and operating rooms is similarly limited. For this reason, postinstallation testing of such equipment and facilities is generally limited to determining whether filters, duct systems, air flows and air movers are operating according to specifications, but cannot assure that the equipment as a whole is operating as intended.

There is accordingly a need for a simple, sensitive airborne particle detection technique which obviates the risk of contamination by live microorganisms and can be conducted readily at the site of installation of the equipment or installation being tested. It is an object of the invention to provide a family of such tests. Another object is to provide test kits for use in detecting leaks of airborne microorganism and other particles in equipment including gas movement apparatus after installation of the apparatus and at intervals thereafter for maintenance purposes. Still another object is to provide tests of the type described which may be correlated with the accepted Bacterial Aerosol Tracer test.

These and other objects of the invention will be apparent from the description, drawing, and claims which follow.

SUMMARY OF THE INVENTION

The instant invention comprises a process and test kit for determining the reliability of a barrier to microorganism passage in apparatus such as biological containment hoods, and air conditioning systems, heating systems, and other building installations. In accordance with the process of the invention, a multiplicity of non-selfreplicating particles is introduced into a first gas volume, disposed on one side of an intended barrier to particle movement, and particle traps are placed in a second gas volume on the other side of the barrier. The barrier may comprise an air curtain, seal, filter, or the like. The non-selfreplicating particles carry a marker substance capable of enabling detection of less than 100, preferably less than 25 of the particles and are of a size comparable to the microorganism sought to be confined by the barrier. The apparatus being tested is then operated, and the contents of the trap are assayed for the amount of the substance used as a particle marker. Finally, the results of the assay are compared to a standard to determine the number of trapped particles which have crossed the barrier.

Preferably, the non-selfreplicating particles comprise killed microorganisms such as killed bacterial spores, but latex particles may also be used. The marker substance may comprise a catalyst, in which case the assay is conducted employing a substrate solution or other reactants and detecting the presence of products produced by the action of the catalyst. Alternatively, the particle marker substance may comprise a toxin for a selected microorganism. In this case the assay is conducted by culturing the microorganism in the presence of toxin associated with the contents of the particle trap and detecting the extent of death of the culture. The currently preferred particle marker substance comprises a component needed for growth of a selected microorganism on a selected medium. In this case the assay is conducted by adding component, if any, that is associated with the contents of the trap to a culture of the selected microorganism and detecting its extent of growth. Preferred essential components used as a marker include nutrients, enzymes, and plasmids. The currently most preferred marker substance is a vitamin such as niacin. When niacin is used, the assay may be conducted using a static, niacin-starved culture.

Various assay techniques may be employed depending on the design of the system. For example, the assay may involve measurement of the amount of product in a reaction involving the marker substance, or the measurement of a quantity proportional to the amount of product such as pH or optical density. The preferred embodiments of the process of the invention enable the detection of as few as ten particles and most preferably enable detection of a single particle.

The test set of the invention comprises a multiplicity of non-selfreplicating particles each of which carry a marker substance. The particles are of a size comparable to the microorganism sought to be confined by the barrier. The test set further includes means for assaying for the substance which can indicate the presence of a collection of at least 100, and preferably at least 25 particles, and a standard for correlating the results of the assay to the number of particles present in the trap or traps.

BRIEF DESCRIPTION OF THE DRAWINGS

The sole FIGURE of the drawing is a curve of pH versus micrograms of niacin of the type useful as a standard in accordance with one embodiment of the invention.

DESCRIPTION

Figure 1:
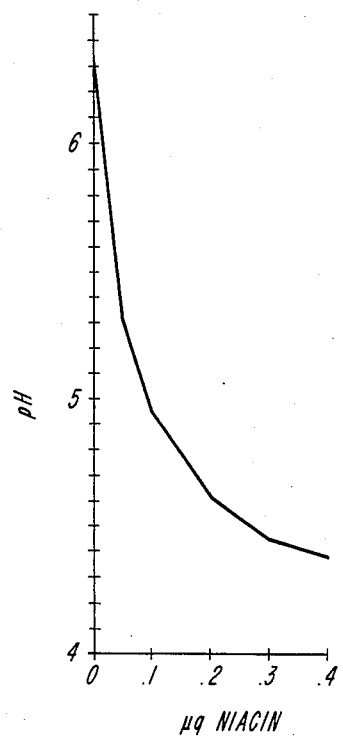

The process and test set of the invention broadly are designed to test the reliability of barriers intended to limit or prohibit the movement of airborne microorganisms from one volume of air (or other gas) to another. Examples of such barriers include air curtains formed by directed air streams and baffles in biological and other types of containment cabinets, filters in air conditioning and forced air heating systems, and seals about ductwork, plenums, cooling towers, and related equipment. The process and test set of the invention may be used, for example, to determine the extent to which an installed biological containment cabinet permits leakage of airborne microorganisms from the workspace site into the ambient environment, or conversely, permits the introduction of external airborne particles into the workspace. The invention may also be used to test for leakage of microorganisms at points outside a containment installation, e.g., those constructed in connection with genetic engineering laboratories and clean rooms employed in the fabrication of solid state devices or used in connection with health care facilities.

There are several reasons why conventional bacterial aerosol tracer tests employing live microorganisms have limited use in testing these types of facilities. First, the conventional tests inherently involve the risk of contaminating workspace with countless live microorganisms that may be difficult to kill or remove. Second, there is a finite probabililty that the organism used for testing may already be present in the air volume where the traps are located. This can lead to false positive results if one or more of the ambient microorganisms are trapped during the assay.

The broad approach of the invention involves the use of non-selfreplicating particles in place of the live microorganisms normally employed. Preferably, the particles are of a size comparable to the microorganism that are to be confined, and otherwise simulate the density and aerodynamic properties of such organisms so that their transport in air simulates the transport of the airborne microorganisms. Preferably, the particles comprise killed intact microorganisms such as killed bacterial spores, killed bacterial or yeast cells, or killed virus particles. If the microorganisms to be confined vary in size, it may be desirable to likewise vary the size of the test particles. In general, any type of suitably-sized particles may be employed. An example is latex particles. Preferably, the particles are introduced into the space during the test as a fog, smoke, or aerosol.

Use of such non-living particles in airborne particle analysis is feasible only if a method is developed for reproducibly detecting the presence of small numbers of particles. In general, detection methods that require collection of 100 or more particles before reproducible results are obtained are unsuitable for the relatively demanding applications discussed above. In fact, reproducible detection of less than 10 particles, and preferably a single particle, is very desirable if not essential in efficacy testing of biological containment cabinets.

In accordance with the invention, a substance having the properties set forth below is adsorbed, absorbed, coated, or otherwise associated with the particles as a particle marker. While many types of marker substances potentially can be used, it is essential that the substance be able to provide a biological, chemical, or physical "signal" which during the assay for particles can be "amplified" in some way to permit detection of a small number of particles, e.g., at least about 1 to 25. Furthermore, the substance must be present in association with each particle in the large number used within relatively narrow weight ranges. The substance should also be relatively nonvolatile, i.e., it should not evaporate into the air during the test or prior to the assay, and it should not itself interject a significant health or other risk into the site of use.

Broadly, at least three types of substances may be used to mark the particles: catalysts, cell toxins, and components needed for growth of a particular type of cell in a given medium.

The use of any of these types of systems requires the construction of a standard curve or other means correlating detectable product, cell growth, or cell death (or a quantity proportional to these data such as optical density or pH) to the number of particles carrying the marker that was added to the system.

The assay may be conducted by spraying particles into, e.g., the workspace of a hood, and after operation of the apparatus being tested, mixing the contents of a trap disposed in a test area, or the marker substance associated with the trap contents, with a standard reaction system. The reaction is allowed to proceed under standardized conditions, and then a reading is taken. Lastly, the reading is compared to the standard curve to determine the number of particles that were trapped.

The term "catalyst" as used herein includes enzymes, coenzymes, ATP, and synthetic catalysts which promote a conversion of selected reactants to detectable products. Because such catalysts are themselves not consumed during reaction or are capable of initiating a cascade of reactions in a suitable reaction system, a determination of the amount of catalyst in a given reaction can be made by detecting the amount of product produced in a given time period. Very small amounts of catalyst may be detected because of the ease of detecting a much larger quantity of product. The "signal" provided by the catalyst is thus "amplified" by the catalyzed reaction.

Regarding cell toxins, a number of substances are currently available which at extremely low concentration are capable of destroying large numbers of specific cell types. Examples include selected antibiotics which rapidly destroy microorganisms supersensitive to the antibiotic, and bacterial toxins which at low concentrations kill large numbers of cells in animal cell cultures. Embodiments of the process and test kit of the invention using this type of particle marker involves the use of the toxin disposed on the particles and an assay in which the contents of the trap are incubated with cells sensitive to the toxin. A standard curve or other means correlating observed cell death to the number of particles in the culture should be constructed to intepret the results.

The currently preferred detection system for use in the practice of the invention comprises a component essential for growth of a particular cell type in a particular medium, and a culture of cells in the medium. The "signal" provided by the component in this case is "amplified" to detectable levels by inducing cell growth. Such growth may be observed directly using a nephelometer or the like or measured indirectly by assaying, directly or indirectly, for the presence of a product of cellular metabolism. Examples of suitable components include essential nutrients, enzymes, vitamins, and plasmids. Cultures deficient in the nutrient enzyme or vitamin, or deficient in an essential growth component the cells cannot themselves produce without transfection of a suitable plasmid, may be used to detect and quantify the presence of one or more particles.

To conduct a test using this type of system, a static culture preferably is used which has been grown in the absence of the essential component until expansion of the number of cells in the culture has terminated. Particles containing the essential component are sprayed or otherwise introduced into the air volume in which the microorganism is to be confined, and one or more particle traps are disposed in air volumes into which microorganisms potentially can leak. For example, the particles may be sprayed into the workspace of a biological containment hood, and traps can be located in regions outside the air curtain. The hood is then operated, and thereafter the contents of the trap are added to the static cultures. If a particle traverses the barrier and is collected in the trap, the component associated with the particle initiates cell growth in the culture. The amount of growth is measured, directly or indirectly, and then the results are compared to a standard to determine the number of particles which escaped.

If an enzyme, vitamin, or essential nutrient is used, it is absorbed by the cells and triggers cell division which is detected. A plasmid may be used in connection with a culture disposed in a medium lacking a growth component or containing a growth restraining component. Plasmid carried by the trapped particles is transfected into the cells and provides genetic information which permits them to grow in the medium. Thus, the plasmid may include DNA encoding an enzyme which destroys the growth restraining component or encoding the factor missing from the medium. In either case, cell growth is possible only if the plasmid is incorporated in the cell's genome, and since the only source of the plasmid is trapped particles, the amount of growth may be correlated with the number of escaping particles.

Those skilled in the art will be able to design specific systems using such particle markers and suitable detection systems in view of the foregoing disclosure, the example which follows, and the literature which discloses sources and the properties of many suitable enzymes, coenzymes toxins, nutrients and other potentially useful marker substances. Other systems in addition to those described above may be used. For example, ATP may be used with detection taking place in bioluminescent reactions. Bacterial endotoxins may be used with detection taking place in a reaction wherein limulus lysate coagulates.

The constructions of a standard curve or other means for correlating the results of the assay to the number of particles may be done in several ways. Generally, the approach is to run numerous tests using a standardized protocol and a known number of particles, and then to construct a table or curve correlating the number of particles to the assay results. Increasing numbers of particles carrying the nutrient, plasmid, cell toxin, etc., that are to be used in the assay may be added directly to the assay system and the assay results directly correlated with the particle count. It is also possible to construct a standard curve and to correlate the test with the accepted Bacterial Aerosol Test in a single operation. In this case live microorganisms carrying the particle marker are used to conduct a test, e.g., in a biological containment hood before installations. After the particles in the traps are separated from the marker substance, the marker substance is added to the test system, and the assay conducted. The live microorganisms are cultured in the normal way to determine the number of organisms which escaped the hood, e.g., by culturing using the standard Bacterial Aerosol Traser test procedure. This permits the results of the assay, and thus the results of the test conducted in accordance with the invention, to be correlated with the results obtained in the prior art test.

The invention will be understood further from the following non-limiting example.

A test set and procedure embodying the invention was designed using killed bacterial spores suspended in a niacin solution, with a niacin starved inoculum of lactobacillus as the means for detecting the niacin and determining the number of escaping particles. The procedure was used to test the integrity of an air curtain in a biological containment cabinet after construction of a standard curve. Details of the materials used and the test protocol are set forth below.

Preparation of Reagents

One hundred milligrams of niacin were dissolved in one liter of distilled water and subsequently serially diluted as necessary to make stock dilute niacin solutions. Autoclaved bacillus spores (Bacillus subtilis var. niger, ATCC No. 9372) were mixed with a 100 microgram/ml niacin solution to produce a killed spore suspension containing about $5 \times 10^8$ to $9 \times 10^8$ killed spores per milliliter of solution. Killed lactobacillus arabinosa or Lactobacillus plantarum may also be used.

A niacin-free lactobacillus medium was prepared by boiling 1.5 g dehydrated ADAC broth (Difco) in 100 ml distilled water. A niacin-starved lactobacillus culture (Lactobacillus plantarum, ATCC No. e8014) was prepared by serially passing the lactobacillus through 10 ml aliquots of medium until no growth was observed. The culture just prior to the last passage was used as the test culture for determining the number of particles escaping the hood.

Five standard curve tubes were prepared containing 5 ml of the niacin assay medium and 0, 0.05, 0.1, 0.2, and 0.3, micrograms niacin per tube, respectively, diluted with distilled water to a volume of 10 ml.

Test Setup

A stainless steel "arm", 2.5 inches in diameter, was fixed centrally in the workspace of a biological containment hood, 2.75 inches above the work surface and extending from the back of the work area through the air curtain and 6 inches beyond. A nebulizer having a capacity of approximately 55 ml of the spore suspension was placed in the workspace of the hood with its output nozzle disposed directly above the arm, 14 inches above the work surface and 4 inches behind the view screen.

Six particle traps were disposed outside the hood: two, 12 inches apart and two inches back from the air curtain at the same height as the nebulizer; two, six inches apart and 2½ inches from the face of the cabinet tangent with the top of the arm; and two, two inches apart, 2½ inches from the face of the cabinet, and one inch below the arm. Each trap comprised a flask containing approximately 20 ml of distilled sterile water fitted with a tube and an aspirator for drawing air and any spores it contains through the water. The traps are chemically cleaned before use.

As a positive control, a plate seeded with niacin-starved lactobacilli and a pH indicator was placed within the workspace of the hood supported one quarter inch above the front perforated grille and directly below the arm.

Construction of Standard Curve

Live bacillus spores were mixed with a 100 microgram/ml niacin solution to produce a live spore suspension. About 55 milliliters of the suspension were loaded into the nebulizer. The cabinet was turned on and operated at least 30 minutes before the nebulizer was run for 16.5 minutes at 20 psi. One minute after nebulizer activation, the traps were set to draw approximately 12.5 liters of air/minute through the distilled water for 15 minutes. After 25 minutes of hood operation, the liquid from all six traps was quantitatively filtered through a 0.22 micron filter to remove the live spores, if any, trapped in the distilled water. The number of live spores contained on the filter was determined by incubating the filter residue with trypticase soy agar and determining the number of colonies formed. The filtrate, containing the niacin that had been adsorbed on the live spores, was then mixed with the niacin-free lactobacillus medium and boiled to assure dissolution of the medium. Then both the resulting filtrate (mixed with medium) and the five standard curve tubes were autoclaved together for 10 minutes at 15 psi at 121° C. The flask and standard curve tubes were then inoculated with the niacin-starved lactobacillus culture (passage before zero growth) and incubated for 72 hours. Since the amount of growth of lactobacilli is inversely proportional to the pH of the medium, the pH may be measured in each of the five tubes and the results plotted against micrograms of niacin to obtain a curve useful in determining the number of micrograms of niacin in the flask. Thus the pH of the flask is measured, and from this datum the amount of niacin in the traps is determined by extrapolations from the curve. A typical curve is shown in FIG. 1. Since the number of spores which carried this amount of niacin is known, one can make a direct correlation between the pH in the test medium inoculated with starved lactobacillus and the number of particles traversing the air curtain during the test. This permits the construction of a performance data chart. For one series of runs, the performance data chart was as follows.

| Microgram Niacin Observed in Traps | Number of Escaping Particles | Estimated Hood Performance |
|---|---|---|
| 0.0 | 0 | Excellent |
| 0.0–0.025 | 1–2 | Good |
| 0.025–0.05 | 2–10 | Poor |
| 0.05 | >10 | Not properly functioning |

Tests of installed hoods and other containment devices may be conducted without risk of contaminating the site of the installation by following the protocol set forth above described in connection with the construction of a standard curve, except that the killed spore suspension is used in the nebulizer in place of the live spore suspension. By measuring the pH of the incubated trap contents, the number of micrograms of niacin it contains can be determined, and this can be directly correlated with the number of particles which escaped.

The invention may be embodied in other specific forms without departing from the spirit and scope thereof. Accordingly, other embodiments are within the following claims.

What is claimed is:

1. A process for testing the reliabiity of a barrier for prohibiting the passage of airborne microorganisms from a first gas volume to a second gas volume, the process comprising the steps of:
   A. introducing into a first gas volume a multiplicity of non-self replicating particles carrying a marker substance, said marker substance being selected from the group consisting of a toxin for a selected microorganism and a component needed for growth of a selected microorganism;
   B. placing a particle trap in a second gas volume;
   C. operating the barrier;
   D. thereafter, assaying for the amount of said marker substance present in association with particles which crossed said barrier, and which are contained in said particle trap; by adding the marker substance associated with the contents of said trap to a culture of said selected microoganism, said culture being capable of detecting the presence of less than 10 of said particles, and detecting the effect of said marker substance on said culture; and
   E. comparing the results of step D to a standard to determine the number of particles which crossed said barrier.

2. The process of claim 1 wherein said barrier comprises a biological containment hood.

3. The process of claim 1 wherein said barrier comprises an air curtain.

4. The process of claim 1 wherein said particles comprise killed microorganisms.

5. The process of claim 1 wherein said particles comprise latex particles.

6. The process of claim 1 wherein said marker substance comprises a toxin for said selected microorganism, and step D comprises the step of adding the toxin associated with the contents of said trap to a culture of said selected microorganism and detecting the extent of the death of cells in said culture.

7. The process of claim 1 wheren said marker substance comprises a component needed for growth of said selected microorganism in a selected medium, and step D comprises the step of adding the component associated with the contents of said trap to a culture of said selected microorganism and detecting the extent of growth therein.

8. The process of claim 7 wherein said component needed for growth is selected from the group consisting of nutrients, enzymes, vitamins, and plasmids.

9. The process of claim 7 wherein said component needed for growth comprises niacin, and said culture of said selected microorganism is a static, niacin-starved culture.

10. The process of claim 9 wherein said standard comprises means for correlating the extent of growth of said niacin-starved culture to the number of particles contained in said trap.

11. The process of claim 1 wherein said culture is capable of detecting a single one of said particles.

12. The process of claim 11 wherein said marker substance is niacin, and said step of adding in step D comprises adding niacin associated with the contents of said trap to a niacin-starved culture.

13. The process of claim 12 wherein said step of adding in step D comprises the step of measuring the pH of said niacin-starved culture and said step of comparing in step E comprises comparing the measured pH to a standard correlating pH to the number of particles trapped.

14. The process of claim 13 wherein said niacin-starved culture is a lactobacillus culture.

15. A test kit for testing the reliability of a barrier for prohibiting the passage of airborne microorganisms from a first gas volume to a second gas volume, said kit comprising:

a multiplicity of non-self replicating particles carrying a marker substance, said marker substance being selected from the group consisting of a toxin for a selected microorganism and a component needed for growth of a selected microorganism;

means for assaying for said marker substance, said means being capable of detecting the presence of a collection of less than 10 of said particles and comprising a culture of said selected microorganism;

means for correlating the results of an assay for said marker substance to the number of said articles associated with said marker.

16. The kit of claim 15 wherein said means for assaying is capable of detecting the presence of a single one of said particles.

17. The kit of claim 15 wherein said particles are selected from the group consisting of killed microorganisms and latex particles.

18. The kit of claim 15 wherein said marker substance comprises a toxin for said selected microorganism.

19. The kit of claim 15 wherein said marker substance comprises a component needed for growth of said selected microorganism in a selected medium.

20. The kit of claim 19 wherein said component needed for growth is selected from a group consisting of nutrients, enzymes, vitamins, and plasmids.

21. The kit of claim 19 wherein said component needed for growth is niacin, and said culture of said selected microorganisms comprises a niacin-starved culture.

* * * * *